United States Patent
Ritchie et al.

[11] Patent Number: 6,048,998
[45] Date of Patent: Apr. 11, 2000

[54] ONE-STEP PROCESS FOR PREPARING METHYL 2-(HALOMETHYL) PHENYLACETATE FROM 3-ISOCHROMANONE

[75] Inventors: David John Ritchie; Hannah Sallie Robertson McCann, both of Stirlingshire, United Kingdom; Michael Charles Henry Standen, Bucks, Ala.; Raymond Vincent Heavon Jones, West Lothian, United Kingdom

[73] Assignee: Zeneca Limited, United Kingdom

[21] Appl. No.: 09/202,345

[22] PCT Filed: May 21, 1997

[86] PCT No.: PCT/GB97/01390

§ 371 Date: Dec. 14, 1998

§ 102(e) Date: Dec. 14, 1998

[87] PCT Pub. No.: WO97/48671

PCT Pub. Date: Dec. 24, 1997

[30] Foreign Application Priority Data

Jun. 17, 1996 [GB] United Kingdom .................. 9612622

[51] Int. Cl.$^7$ ........................................................ C07C 69/76
[52] U.S. Cl. ....................................................... 560/8; 560/1
[58] Field of Search ............................................... 560/1, 8

[56] References Cited

FOREIGN PATENT DOCUMENTS

| 0 278 595 B1 | 11/1992 | European Pat. Off. . |
| 0 676 389 A2 | 4/1995 | European Pat. Off. . |
| 0 583 589 B1 | 6/1996 | European Pat. Off. . |
| 59-163370 | of 1984 | Japan . |
| WO 95/25729 | 3/1995 | WIPO . |

OTHER PUBLICATIONS

Chemical Abstracts, Rn 13737–37–6, 1997.
Chemical Abstracts, vol. 92, 180829h 1980.
Chemical Abstracts, vol. 92, 128526t 1980.

*Primary Examiner*—Gary L. Kunz
*Attorney, Agent, or Firm*—David P. LeCroy

[57] ABSTRACT

Methyl 2-(chloro- or bromomethyl)phenylacetate is prepared by treating 3-isochromanone with thionyl chloride or thionyl bromide in the presence of methanol.

9 Claims, No Drawings

ONE-STEP PROCESS FOR PREPARING METHYL 2-(HALOMETHYL) PHENYLACETATE FROM 3-ISOCHROMANONE

This invention relates to a chemical process and more particularly to a process for preparing methyl 2-(chloro- or bromomethyl)phenylacetate which is useful as an intermediate in the manufacture of agricultural compounds.

The compound methyl 2-(chloromethyl)phenylacetate and its method of preparation from o-xylene, via 2-methylphenyl acetonitrile and 2-methylphenyl acetic acid, is disclosed in JP 59-163370 A.

A method of preparing methyl 2-(haloalkyl) phenylacetates, such as the 2-bromoalkyl compounds, by ring opening isochromanones using a hydrogen halide in methanol is mentioned in EP-A-278595. The ring opening of 3-isochromanone using hydrogen bromide is also mentioned in CA 92: 128526t and CA 92: 180829h. However, in both these references the free 2-(bromomethyl)phenylacetic acid is said to be formed, the isochromanone ring being cleaved with either $HBr-H_2SO_4$ or HBr in acetic acid.

The preparation of methyl 2-[2-(halomethyl)phenyl]-3-methoxypropenoates by reacting 4-(α-methoxy)methylene-2H-chromen-3(4H)-one with a thionyl halide optionally in the presence of a solvent and reacting the product so formed with methanol, is described in WO 95/25729. In specific examples, 4-(α-methoxy)-methylene-2H-chromen-3(4H)-one is reacted with refluxing thionyl chloride. At the end of reaction, excess thionyl chloride is removed and the product so formed then reacted with methanol.

The present invention provides an industrially suitable, one-stage process for the preparation of methyl 2-(chloro- or bromomethyl)phenylacetate from 3-isochromanone which can be carried out at moderate temperatures and which offers environmental advantages in terms of the lower generation of unwanted methyl chloride or methyl bromide by-product.

Thus, according to the present invention, there is provided a process for preparing a methyl 2-(halomethyl) phenylacetate which comprises treating 3-isochromanone with a thionyl halide of formula $SOX_2$ wherein X is chlorine or bromine, in the presence of methanol.

The process, which is represented by the reaction scheme:

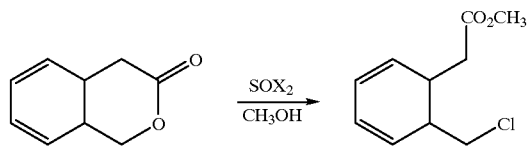

may be carried out at a temperature of from −80° C. to 130° C. (under pressure), for example, from −40° C. to 40° C., and typically from 0° C to 30° C. Normally it is carried out keeping the temperature just below 25° C. It is an advantage of the invention process that it can be operated at ambient temperatures.

The amount of thionyl halide used may range from 0.5 moles per mole of isochromanone to any sensible upper limit consistent with practicality. Normally it is in the range of from 1.0 to 2.1 moles per mole of isochromanone and preferably from 1.15 to 1.65. Typically it is about 1.25 moles per mole of isochromanone.

The amount of methanol used may range from 1 mole per mole of isochromanone to any upper limit consistent with practicality. Preferably it is in the range of from 3 to 3.5, typically 3.05 to 3.1 moles per mole of isochromanone.

Normally the invention process is carried out with a suitable diluent. Suitable diluents include methanol and other solvents, such as saturated or aromatic hydrocarbons or their fluorinated or chlorinated derivatives, which are inert to the reactants. When methanol is used as diluent, the total amount of methanol present (diluent and reactant) is, for example, from 9 to 10 moles per mole of isochromanone, typically from 9 to 9.1. For industrial purposes, toluene is a very convenient diluent.

Thus, in one aspect, the invention provides a process for preparing a methyl 2-(halomethyl)phenylacetate which comprises treating 3-isochromanone with 1.0 to 2.1 moles of a thionyl halide of formula $SOX_2$ (wherein X is chlorine or bromine) per mole of 3-isochromanone in the presence of from 3 to 3.5 moles of methanol per mole of 3-isochromanone in a suitable diluent and at a temperature of from 800° C. to 130° C.

Suitably from 1.15 to 1.65, and more suitably about 1.25, moles of thionyl halide per mole of 3-isochromanone are used.

Suitably from 3.05 to 3.1 moles of methanol per mole of 3-isochromanone are used.

The diluent is either methanol itself or a saturated or aromatic hydrocarbon or a chlorinated derivative thereof. Typically, it is methanol or toluene.

Suitably the temperature at which the process is carried out is −40° C. to 40° C., preferably 0° C. to 30° C.

In a typical process, the 3-isochromanone is slurried in the diluent and the methanol then added. Where methanol is used as the diluent, the isochromanone is slurried in all of the methanol (i.e. reactant and diluent combined). The thionyl halide is added during, for example, 2–3 hours, and the temperature maintained in the desired range. The progress of the reaction is monitored by analysing samples of the reaction mixture at suitable intervals using gas chromatography and is adjudged complete when the 3-isochromanone content falls, for example, to below 1%. At the end of reaction, the reaction mixture is neutralised with, for example, an aqueous solution of potassium bicarbonate and the organic and aqueous layers separated and washed. The product is isolated by drying and distilling off the diluent from the organic phase or, where, toluene is used as the diluent, by azeotropically distilling off residual water and toluene.

The starting material, 3-isochromanone, is a commerically available product.

A benefit of the invention process is that much less undesirable methyl chloride or bromide is formed than when reacting 3-isochromanone with dry hydrogen chloride or bromide and methanol. With the added benefit that it can be operated at ambient temperature, the process is particularly suited to large scale, industrial use.

The product of the process, methyl 2-(halomethyl) phenylacetate is useful, inter alia, as an intermediate in the manufacture of agricultural products, especially fungicides of the strobilurin type, for example those described in EP-A-278595 and EP-A-370629. Such compounds include those of the formula:

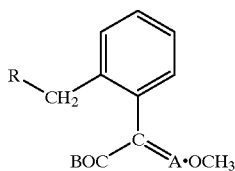

in which A is CH or N, B is OCH$_3$ or NHCH$_3$ and R is the residue of an organic group.

The invention is illustrated by the following Examples in which g=grammes GC=gas chromatography
mol=moles ° C.=degrees Centigrade
s=singlet m=multiplet
NMR=nuclear magnetic resonance
ppm=parts per million

EXAMPLE 1

Diluent: methanol
Thionyl chloride: 2.1 equivalents
Temperature: ambient

3-Isochromanone (15 g, 0.099 mol) was charged to methanol (30.2 g, 0.9 mol) in a 100 ml round bottom flask and the temperature lowered to <10° C. Thionyl chloride (25 g, 0.21 mol) was added dropwise maintaining the temperature at −5° C. to 0° C. The reaction mixture was stirred, allowing the temperature to rise to ambient for 2 hours then tested for completion of reaction by GC analysis (completed when <1% 3-isochromanone left). The product was extracted with toluene and washed with water followed by dilute potassium bicarbonate solution until pH>6. The toluene was removed by vacuum distillation to ca. 10% toluene by area % GC analysis. The final product, methyl 2-(chloromethyl)phenylacetate, was weighed and analysed by GC: 16.9 g (18.2 g at 93.03% strength), 85% yield; 2.23% methyl 2-(methoxymethyl) phenylacetate impurity; no 3-isochromanone starting material detected.

EXAMPLE 2

Diluent: methanol
Thionyl chloride: 1.25 equivalents
Temperature: <25° C.

3-Isochromanone (1 equivalent) was slurried in methanol (9.1 equivalents) and the slurry temperature maintained below 25° C. Thionyl chloride (1.25 equivalents) was added over approximately 3 hours keeping the temperature below 25° C. The reaction mixture was analysed qualitatively by GC indicating that the residual 3-isochromanone content was less than 2%. The brown reaction solution was slowly added to an excess of 20% potassium bicarbonate solution and the aqueous and organic layers stirred for ½ hour, allowed to settle for 1 hour and then separated. The aqueous layer was washed with toluene and the organic layers were combined and given two water washes. The combined organic material was distilled to azeotrope water and reduce the toluene content to approximately 10%. The final product, methyl 2-(chloromethyl)phenylacetate, was weighed and analysed quantitatively by GC: strength 90%, yield 85%; residual 3-isochromanone content <10%; methyl 2-(methoxymethyl)phenylacetate impurity of 2%.

EXAMPLES 3–7

These Examples were carried out using the same reaction procedure as described in Example 2 except as indicated below.

EXAMPLE 3 thionyl chloride 1.3 equivalents; methanol 9.0 equivalents; temperature +40° C. 76.7% Conversion by GC area; residual 3-isochromanone 15%; methoxymethyl impurity 6.6%.

EXAMPLE 4 thionyl chloride 1.25 equivalents; methanol 3.1 equivalents; diluent toluene. 97.9% Conversion by GC area; residual 3-isochromanone 0.1 %; methoxy impurity 1.2%.

EXAMPLE 5 thionyl chloride 1.25 equivalents; methanol 3.05 equivalents; diluent toluene; temperature −40° C. for 1¾ hours.
43.8% Conversion by GC area; residual 3-isochromanone 52.2%; methoxymethyl impurity <1%.

EXAMPLE 6 thionyl chloride 1.65 equivalents; methanol 3.1 equivalents; diluent toluene. 95.8% Conversion by GC area; residual 3-isochromanone 1.4%; methoxymethyl impurity 0.8%.

EXAMPLE 7 thionyl chloride 1.0 equivalents; methanol 3.1 equivalents; diluent toluene; 4 hours at ambient temperature.
84.8% Conversion by GC area; residual 3-isochromanone 12.13%; methoxymethyl impurity 1.72%.

The addition of a further 0.1 equivalent of thionyl chloride stirring at ambient temperature overnight gave 94.9% conversion by GC area; residual 3-isochromanone 1.9%; methoxymethyl impurity 1.9%.

The product was isolated by working up with 20% potassium bicarbonate solution and distillation of the separated organic layer to give a brown oil; 86% quantified yield by GC area %.

EXAMPLE 8

Diluent: toluene
Thionyl bromide: 1.25 equivalents
Methanol: 3.0 equivalents
Temperature: 25° C.

3-Isochromanone (1 g at 100% weight; 1 equivalent) was charged to toluene and methanol (0.65 g at 100% weight; 3 equivalent) added. Thionyl bromide (1.7 g at 100% weight; 1.25 equivalent) was charged at below 30° C. and the reaction held at 25° C. for 3 hours. The reaction mixture was analysed by qualitative GC indicating 23.6% residual 3-isochromanone and 69.5% peak at 7.9 minutes. The reaction mixture was added slowly to an excess of 20% potassium bicarbonate solution and the aqueous and organic layers stirred for 15 minutes, settled and then separated.

The aqueous layer was washed with dichloromethane and the inorganic layers were combined and given two water washes. The combined organic material was distilled to yield a pale cream oil. Qualitative GC analysis showed 18.8% residual 3-isochromanone and 71.3% methyl 2-(bromomethyl)phenylacetate. The oil was analysed by NMR: δ7.1–7.4 (m)-phenyl, 4.6 ppm (s)—CH$_2$Br, 3.8 ppm (s)—CH$_2$—CO$_2$—, 3.6 ppm (s)—CO$_2$CH$_3$.

We claim:
1. A process for the preparation of a methyl 2-(halomethyl)phenylacetate which comprises treating 3-isochromanone with a thionyl halide of formula SOX$_2$ wherein X is chlorine or bromine, in the presence of methanol.

2. The process according to claim 1 which is carried out at a temperature of from −80° C. to 130° C.

3. The process according to claim 1 in which the amount of thionyl halide used is in the range of from 1.0 to 2.1 moles per mole of 3-isochromanone.

4. The process according to claim 1 in which the amount of methanol used is in the range of from 3 to 3.5 moles per mole of 3-isochromanone.

5. The process according to claim 1 in which there is a diluent present.

6. The process according to claim 5 in which the diluent is methanol or a saturated or aromatic hydrocarbon or a fluorinated or chlorinated derivative thereof.

7. The process according to claim 5 in which the diluent is toluene.

8. The process of claim 1 for the preparation of methyl 2-(chloromethyl)phenylacetate.

9. The process of claim 1 for the preparation of methyl 2-(bromomethyl)phenylacetate.

* * * * *